United States Patent [19]
Wolff et al.

[11] Patent Number: 5,851,217
[45] Date of Patent: Dec. 22, 1998

[54] INTRALUMENAL DRUG ELUTING PROSTHESIS

[75] Inventors: Rodney G. Wolff, Minnetonka Beach; Vincent W. Hull, Ham Lake, both of Minn.

[73] Assignee: Medtronic, Inc., Minneapolis, Minn.

[21] Appl. No.: 430,046

[22] Filed: Apr. 27, 1995

Related U.S. Application Data

[60] Division of Ser. No. 171,361, Dec. 21, 1993, Pat. No. 5,545,208, which is a continuation-in-part of Ser. No. 815,560, Dec. 27, 1991, abandoned, which is a continuation of Ser. No. 486,580, Feb. 28, 1990, abandoned.

[51] Int. Cl.$^6$ ........................................................ A61F 2/06
[52] U.S. Cl. ........................ 606/191; 606/195; 606/198; 623/1; 623/12
[58] Field of Search ...................... 600/36; 606/191–200; 623/1, 11–12

[56] References Cited

U.S. PATENT DOCUMENTS

| | | |
|---|---|---|
| 4,326,532 | 4/1982 | Hammar . |
| 4,650,466 | 3/1987 | Luther . |
| 4,655,771 | 4/1987 | Wallsten . |
| 4,678,466 | 7/1987 | Rosenwald . |
| 4,739,762 | 4/1988 | Palmaz . |
| 4,871,365 | 10/1989 | Dumican . |
| 4,872,874 | 10/1989 | Taheri . |
| 4,886,062 | 12/1989 | Wiktor . |
| 4,892,539 | 1/1990 | Koch . |
| 4,923,470 | 5/1990 | Dumican . |
| 4,944,767 | 7/1990 | Barbucci . |
| 5,015,253 | 5/1991 | MacGregor . |
| 5,019,090 | 5/1991 | Pinchuk .................................. 606/194 |
| 5,019,096 | 5/1991 | Fox, Jr. . |
| 5,028,597 | 7/1991 | Kodama . |
| 5,047,020 | 9/1991 | Hsu . |
| 5,053,048 | 10/1991 | Pinchuk . |
| 5,059,211 | 10/1991 | Stack . |
| 5,061,275 | 10/1991 | Wallsten . |
| 5,061,276 | 10/1991 | Tu et al. ..................................... 623/1 |
| 5,062,829 | 11/1991 | Pryor . |
| 5,102,417 | 4/1992 | Palmaz . |
| 5,152,783 | 10/1992 | Suzuki . |
| 5,152,784 | 10/1992 | Tsilibary . |
| 5,165,919 | 11/1992 | Sasaki . |
| 5,171,262 | 12/1992 | MacGregor . |
| 5,213,580 | 5/1993 | Slepian et al. ............................. 623/1 |

OTHER PUBLICATIONS

Portion of Article in American Journal of Cardiology, p. 19F, Oct. 1, 1988.

*Primary Examiner*—Mary Beth Jones
*Assistant Examiner*—Francis K. Cuddihy
*Attorney, Agent, or Firm*—Daniel W. Latham; Harold R. Patton

[57] ABSTRACT

A prosthesis for insertion into a lumen to limit restenosis of the lumen. The prosthesis carries restenosis-limiting drugs which elute after the device is positioned in the lumen.

73 Claims, 7 Drawing Sheets

INTRALUMENAL DRUG ELUTING PROSTHESIS

This application is a divisional of U.S. Ser. No. 08/171,361, filed Dec. 12, 1993, now U.S. Pat. No. 5,545,208 issued on Aug. 13, 1996 which is a continuation-in-part of U.S. Ser. No. 07/815,560 filed Dec. 27, 1991, now abandoned which is a continuation of U.S. Ser. No. 07/486,580 filed Feb. 28, 1990, now abandoned.

BACKGROUND OF THE INVENTION

1. Field of the Invention

This invention related to methods for lessening restenosis of body lumens, and to prosthesis for delivering drugs to treat said restenosis.

2. Description of the Related Art

Restenosis is defined as the reclosure of a previously stenosed ans subsequently dilated peripheral or coronary vessel. It occurs at a rate of 20–50% for these procedures and is dependent on a number of clinical and morphological variables. Restenosis may begin shortly following an angioplasty procedure, but usually ceases at the end of approximately six (6) months. There is not a current therapeutic procedure that has been proven to significantly reduce this restenosis rate.

A recent technology that has been developed that assesses the problem of restenosis is intravascular stents. Stents are typically metallic devices that are permanently implanted (expanded) in coronary and peripheral vessels. The goal of these stents is to provide a long-term "scaffolding" or support for the diseased (stenosed) vessels. The theory being, if you can support the vessel from the inside, the vessel will not close down or restenose. Unfortunately, initial data from clinical stent implants indicates that these metallic structures are not very successful in reducing restenosis.

Pharmacologic (biochemical) attempts have been made to reduce the rate of restenosis. All of these attempts have dealt with the systemic delivery of drugs via oral, intravascular or intramuscular introduction. Little, if any success has been achieved with this systemic approach.

For drug delivery, it has been recognized for a long period of time that pills and injections may not be the best mode of administration. It is very difficult with these types of administration to obtain constant drug delivery. Patient noncompliance with instructions is also a problem. Through repeated does, these drugs often cycle through concentration peaks and valleys, resulting in time periods of toxicity and ineffectiveness. Thus, localized drug treatment is warranted.

SUMMARY OF THE INVENTION

The invention provides prostheses which may be inserted into a lumen of a body and fixed to the lumen wall adjacent an area needing treatment. Most typically, the lumen will be part of the vascular system which may be subject to restenosis following angioplasty. However, the methods and devices of the invention are also suited to treatment of any body lumen, including the vas deferens, ducts of the gallbladder, prostate gland, trachea, bronchus and liver or any other lumen of the body where medication cannot be applied without a surgical procedure. The invention applies to acute and chronic closure or reclosure of body lumens.

The prostheses of the invention include at least one drug which will release from the device at a controlled rate to supply the drug where needed without the overkill of systemic delivery. The prostheses include means for fixing the device in the lumen where desired. The prostheses may be completely biodegradable or may be bioabsorbable in whole or incorporated into the lumen wall as a result of tissue over growth, i.e., endothelialization. Alternatively, the prostheses may be biostable in which case the drug is diffused out from the biostable materials in which it is incorporated.

The prosthesis comprises a generally flexible tubular body which is fixed against the lumen walls by a mechanical action. The device should not cause an appreciable reduction in the lumen cross-section where inserted. Conventional stent designs which provide an expansion of the vessel are suitable, though not required. In all cases, the prostheses of the invention require the presence of an elutable drug compounded to the prosthesis itself. With conventional metal stents, the invention requires a drug-carrying coating overlying at least a portion of the metal.

The drugs in the prosthesis may be of any type which would be useful in treating the lumen. In order to prevent restenosis in blood vessels, migration and subsequent proliferation of smooth muscle cells must be checked. Platelet aggregation and adhesion can be controlled with antiplatelets and anticoagulants. Growth factor and receptor blockers and antagonists may be used to limit the normal repair response.

The current invention contemplates the usage of any prosthesis which elutes drugs locally to treat a lumen in need of repair. Controlled release, via a bioabsorbable polymer, offers to maintain the drug level within the desired therapeutic range for the duration of the treatment. When "stent" is referred to herein, it may include the classical definition of stents as they are used in intravascular applications. "Stent" used herein also includes any prothesis which may be inserted and held where desired in a lumen. It includes, but is not limited to, structures such as those shown and described in U.S. Pat. No. 4,886,062 to Wiktor.

BRIEF DESCRIPTION OF THE DRAWINGS

A detailed description of the invention is hereafter described with specific reference being made to the drawings in which.

DESCRIPTION OF THE PREFERRED EMBODIMENTS

Restenosis

In the discussion above, a very simple definition of restenosis was given. As a complement to this definition, there are several more clinical definitions. Several of these definitions are listed below:

1. Reduction of minimal luminal diameter to less than 50% of the normal lumen diameter.

2. Loss of at least 50% of the initial gain achieved in angioplasty.

3. Decrease of at least 30% in the lumen diameter compared to post-angioplasty result.

4. A return to within 10% of the pre-angioplasty diameter stenosis.

5. An immediate post angioplasty diameter stenosis of less than 50% that increases to 70% or greater at follow-up.

6. Deterioration of 0.72 mm in minimal luminal diameter or greater from post-angioplasty to follow-up.

7. As for 6, but with a deterioration of 0.5 mm.

These definitions are sued by cardiologists to angiographically define restenosis.

Several hypotheses exist on why and how restenosis occurs. The current, most widely accepted explanation is that restenosis is a natural healing process in response to the arterial injury that occurs during all types of angioplasty procedures. This very complex healing process results in intimal hyperplasia, more specifically migration and proliferation of medial smooth muscle cells (SMC). The problem associated with this arterial healing process is that in some instances, it does not shut off. The artery continues to "heal" until it becomes occluded. It should be noted that restenosis is not a re-deposition of the plaque-like cholesterol material that originally occluded the artery.

The following is a possible scenario for restenosis according to the vessel healing hypothesis. Successful angioplasty of stenotic lesions produces cracking of the plaque, dissection into the media, denudation and destruction of endothelial cells, exposure of thrombogenic collagen, released tissue thromboplastin, and an increased loss of prostacyclin production. All of these lead to the aggregation of active platelets.

Figure 6:
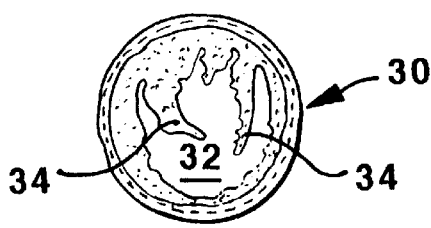
FIG. 6 is a greatly enlarged cross-section of a blood vessel showing plaque profile immediately post-balloon catheter dilation procedure.
Figure 7:
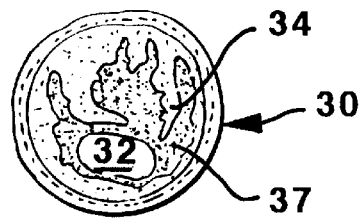
FIG. 7 is a greatly enlarged cross-section of the subject of FIG. 6 at a later date showing restenosis.
Figure 8:
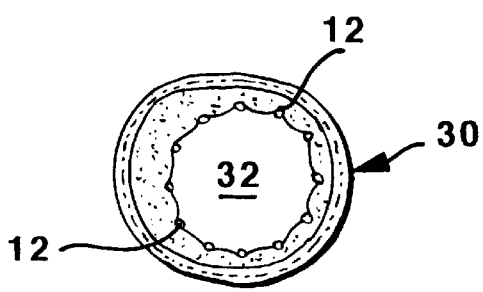
FIG. 8 is a greatly enlarged cross-section of a blood vessel showing plaque-prosthesis profile immediately post-prosthesis implant procedure.
Figure 9:
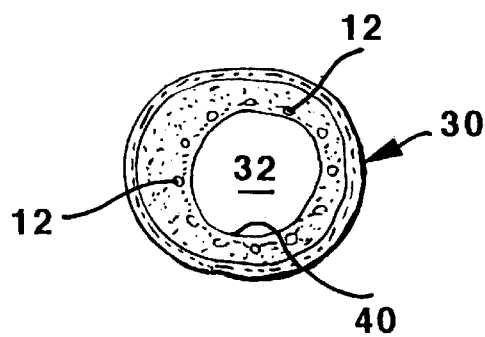
FIG. 9 is a greatly enlarged cross-section of the subject of FIG. 8 after ingrowth has occurred.
Figure 10:
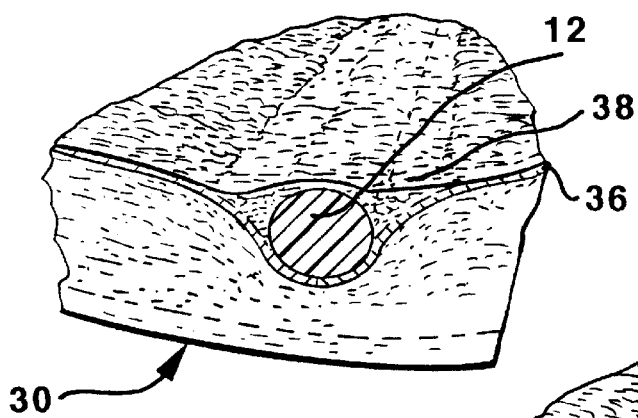
FIG. 10 is a greatly enlarged fragmentary perspective view of a blood vessel wall and prosthesis filament of FIGS. 1 and 3 immediately after implantation.
Figure 11:
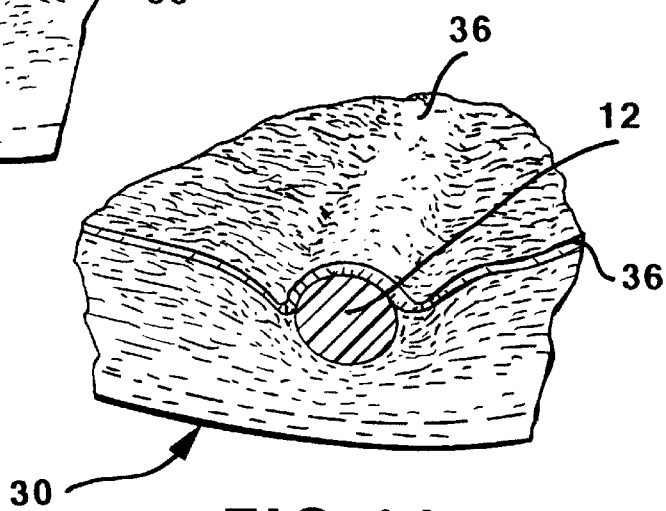
FIG. 11 is a greatly enlarged fragmentary perspective view of the subject of FIG. 10 after about one month.

FIGS. 6 and 7 show a typical vessel 30 in cross-section after angioplasty procedures showing the interior 32 of the lumen. In FIG. 6 the interior of the lumen is rough and includes intimal flaps 34. Damage causes healing with deposition of platelets, fibrin formation and proliferation of neointima 37 which as shown in FIG. 7 significantly reduces the interior of the lumen.

Activated platelets release several mitogens including platelet derived growth factor (PDGF), epidermal growth factor, and transforming growth factor. PDGF has both mitogenic and chemotactic properties and thus, may induce both mitigation of SMC from the medial layer to the intimal layer as well as proliferation (Intimal hyperplasia). PDGF causes SMC proliferation by binding to specific PDGF receptors. Once the PDGF is bound to the receptors, deoxyribose nucleic acid (DNA) synthesis occurs and new cells are replicated. Minor endothelial injury may cause platelet adhesion and activation with the resultant release of PDGF. Thus, even the deposition of a monolayer of platelets may be sufficient to induce SMC proliferation.

Deeper arterial injury which is sometimes associated with complex stenotic lesions leads to more extensive platelet deposition and activation which may cause an even greater availability of the mitogenic factors. Thus, increased SMC proliferation and intimal hyperplasia. Arterial injury from angioplasty may result in release of PDGF-like compounds from not only platelets but also macrophages, monocytes, endothelial cells, or SMC's themselves.

Activated SMC from human atheroma or following experimental arterial injury secrete PDGF-like molecules which appears to lead to self perpetuation of SMC proliferation by the release of their own PDGF-like substances. Thus, any or all of the cells which can secrete PDGF relate substances (platelets, macrophages, monocytes, endothelia, and smooth muscle cells) may contribute to the cascading effect of restenosis after angioplasty.

The previous restenosis scenario resulted from normal angioplasty procedures. During balloon angioplasty if the balloon is undersized or not totally inflated and the plaque cracking and extensive endothelial denudation does not occur the lesion could still restenose. Rheologic factors contribute as well to the interaction between platelets and the arterial Wall. Residual stenosis, resulting from inadequate balloon expansion, produces a high local shear rate and enhances platelet deposition and activation. These stenoses may be important as a stimulus for some proliferation through enhanced platelet deposition and secretion of growth factors. This hypothesis correlates with the increased incidence of restenosis in patients with high-grade residual stenoses or transtenotic gradients.

Prevention of Restenosis

In order to prevent restenosis, one must stop the proliferation of smooth muscle cells. As stated earlier, this is a biochemical process which cannot be treated mechanically. Several hypothesis exist on how to biochemically stop restenosis. Some of which are:

1. Reduce the adhesion and aggregation of the platelets at the arterial injury site.

2. Block the expression of the growth factors and their receptors.

3. Develop competitive antagonists of the above growth factors.

4. Interfere with the receptor signaling in the responsive cell.

5. Find a "natural" inhibitor of smooth muscle proliferation.

Item #1 is directly related to the formation of thrombus, a major problem with all types of angioplasty procedures. Items #2, #3 and #4 are closely related. They deal with blocking restenosis during the massive cell migration and replication cycle. Unlike item #1, these items address the growth factors that are produced from sources other than platelets. Item #5 is listed to address the question; Why don't 50–80% of the people undergoing angioplasty restenose? There may be some type of natural inhibitor that these people produce that stops the proliferation of smooth muscle cells.

There are at least two (2) different ways to prevent the adhesion and aggregation of platelets. One method is to use an antiplatelet and another is to use an anticoagulant.

Antiplatelet drugs include such as aspirin and dipyridamole. Aspirin is classified as an analgesic, antipyretic, anti-inflammatory, antiplatelet drug. It has been clinically tested and proven to reduce the risk of sudden death and/or non-fatal reinfarction in post myocardial infarction (heart attack) patients. The proposed mechanism of how aspirin works, relates directly to the platelets. It somehow blocks the platelets, restricting coagulation. This prevents the cascading platelet aggregation found in thrombus and subsequently restenosis. Aspirin is therefore a possible restenosis inhibitor. Dipyridamole is a drug similar to aspirin, in that is has anti-platelet characteristics. Dipyridamole is also classified as a coronary vasodilator. It increases coronary blood flow by primary selective dilatation of the coronary arteries without altering systemic blood pressure or blood flow in peripheral arteries. These vasodilation characteristics are thought to be possibly beneficial for restenosis prevention.

Anticoagulant drugs include Heparin, Coumadin, Protamine, and Hirudin. Heparin is the most common anticoagulant used today. Heparin, in one form or another, is used in virtually every angioplasty procedure performed. All four (4) of these drugs function as an anticoagulant by preventing the production of thrombin, a binding agent which causes blood to clot. This too, may reduce the cascading effect of platelet aggregation at the lesion site, thus possibly reducing restenosis. The use of Protamine in the presence of Heparin causes the Protamine to function as a Heparin antagonist, blocking the effect of the Heparin. Protamine, however, used alone, acts as an anticoagulant. Hirudin is singled out because it is not normally found in the human body. Hirudin is a drug that is found in the salivary glands of leeches. It is a very concentrated anticoagulant that functions in a similar manner as Heparin, Coumadin, and Protamine.

There are several types of drugs that interrupt cell replication. Antimitotics (cytotoxic agents) work directly to prevent cell mitosis (replication), whereas antimetabolites prevent deoxyribose nucleic acid (DNA) synthesis, thus preventing replication. The action of the antimitotics and antimetabolites are similar, they can be grouped into one category. This category will be known as the anti-replicate drugs.

Anti-replicate drugs include among others: Methotrexate, Colchicine, Azathioprine, Vincristine, VinBlastine, Fluorouracil, Adriamycin, and Mutamycin. The target systemic molarity desired with methotrexate is on the order of $10^{-6}$ M with a range of between $10^{-3}$ to $10^{-8}$ Molar. Locally, the molarity of the drug may be highly variable, which is one of the great disadvantages in systemic administration of the drug. When drugs are delivered locally via the prosthesis of the invention, they may be at therapeutic levels at the diseased site while at the lower limits of detectability in the bloodstream. So little drug is required for effective local treatment of a lumen that the drug may not be detectable in blood samples.

Anti-inflammatory drugs such as glucocorticoids (e.g., dexamethasone, betamethasone) can also be useful to locally suppress inflammation caused by injury to luminal tissue during angioplasty.

If the restenosis process ranges from shortly after injury to about four to six months later, then the generalized elution rates contemplated are such that the drug should ideally start to be released immediately after the prosthesis is secured to the lumen wall to lessen cell proliferation. The drug should then continue to elute for up to about four to six months in total.

Complex systems of drugs may be carried by the prosthesis. An anticoagulant or antiplatelet may be included in the outermost surface of the device in order to elute off very quickly for the first several days. Antiinflammatories and antireplicates can be formulated into the device to continue to elute later, when in contact with non-blood cells after neointima overgrowth has surrounded the device. This usually occurs in about two weeks. The drug elution rate does not need to be uniform, and may be tailored to fit the need of the patient.

Prosthesis (Stent) Design

The current invention contemplates the usage of any prosthesis which elutes drugs locally to treat a lumen in need of repair. When "stent" is referred to herein, it may include the classical definition of stents as they are used in intravascular applications. "Stent" used herein also includes any prosthesis which may be inserted and held where desired in a lumen.

FIGS. 1 through 17 show features of some of the prostheses which may be used to carry and elute restenosis limiting-drugs.

Figure 1:
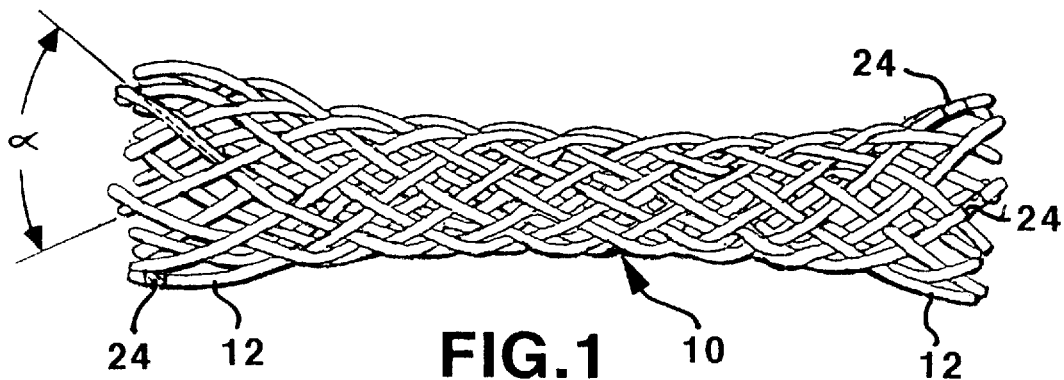
FIG. 1 is a greatly enlarged side view of an intralumenal drug-eluting prosthesis of the invention.

The current preferred stent 10 configuration consists of a single filar, monofilament braided mesh design as shown in FIG. 1. There are sixteen (16) filaments 12, eight (8) of which are wound in one helical direction, and the remaining eight (8) which are wound in the opposite direction. The stent 10 is self-expanding to a predetermined diameter. The profile (diameter) of the stent 10 can be easily reduced by pulling the stent 10 longitudinally. In this reduced profile configuration, the stent 10 can be loaded into a catheter for delivery into the vessel.

Figure 2:
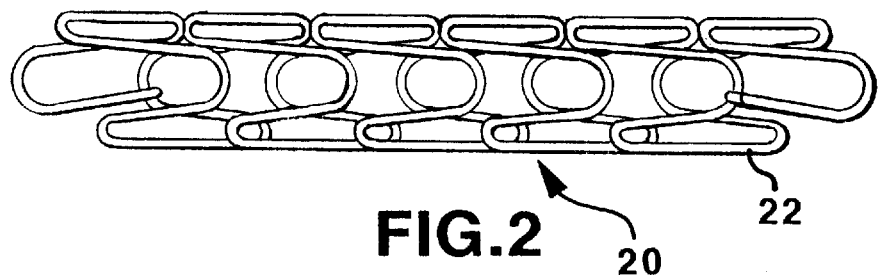
FIG. 2 is a greatly enlarged side view of an alternative embodiment to the prosthesis of FIG. 1.
Figure 4:
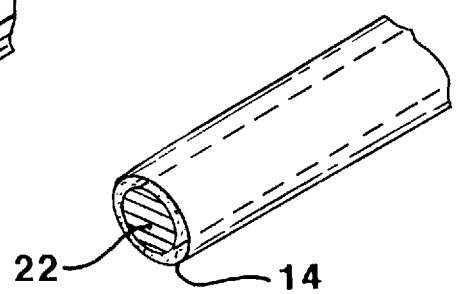
FIG. 4 is a greatly enlarged fragment of the embodiment of FIG. 2.
Figure 5:
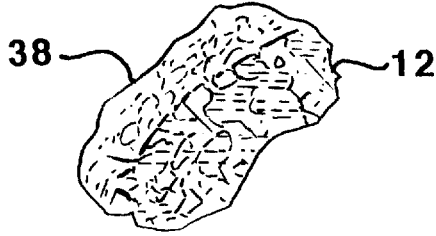
FIG. 5 is a greatly enlarged microscopic fragmentary detail of drug shown eluting form the porous structure of a filament or filament coating in a prosthesis into tissue or the vessel lumen.

The stent 20 shown in FIGS. 2 and 4 is a metallic malleable design which may be forced against a lumen wall by a balloon catheter which fixes it into position. The exterior surface of the metal filaments 22 would include a coating 14 with a drug-eluting polymer described previously. The polymer may be biostable or bioabsorbable. If biostable, the drug would diffuse out of the polymer.

The variations of design shown in the embodiments of FIGS. 1 and 2 show that the prosthesis of the invention must be secured against a lumen wall and must carry a drug-eluting polymer.

There are many variables in the design of stent 10. The angle (a) of the filaments 12 is a major variable. The angle a can vary from 0 degrees to 180 degrees. The design in the Figures is based on an angle in the 60 degree to 90 degree range.

Figure 16:
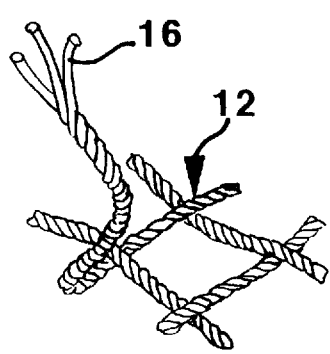
FIG. 16 is a greatly enlarged fragment of multistrand weave of prosthesis filaments.
Figure 17:
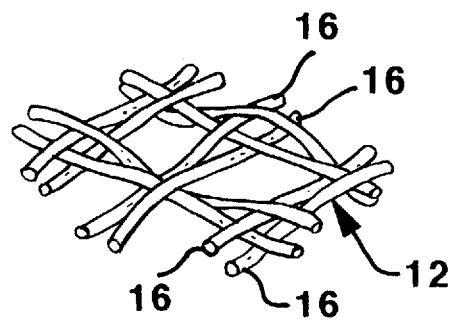
FIG. 17 is a alternative embodiment to FIG. 16, in which strands are not woven.
Figure 18:
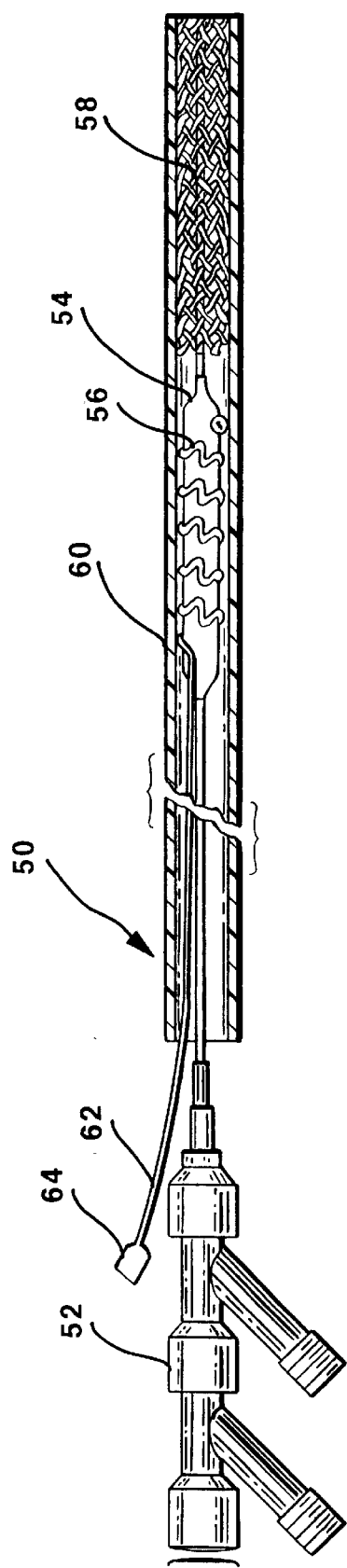
FIG. 18 is a partial sectional view of a catheter for delivery of the prosthesis of the present invention.
Figure 19A:
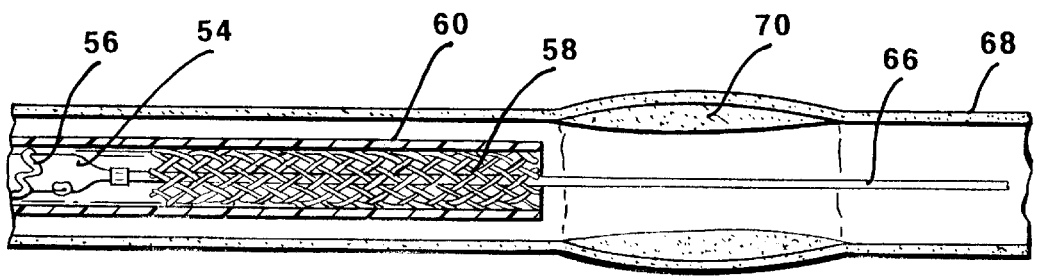
FIG. 19a–19i are sectional views of the deployment of the prosthesis by the catheter of FIG. 18.
Figure 19B:
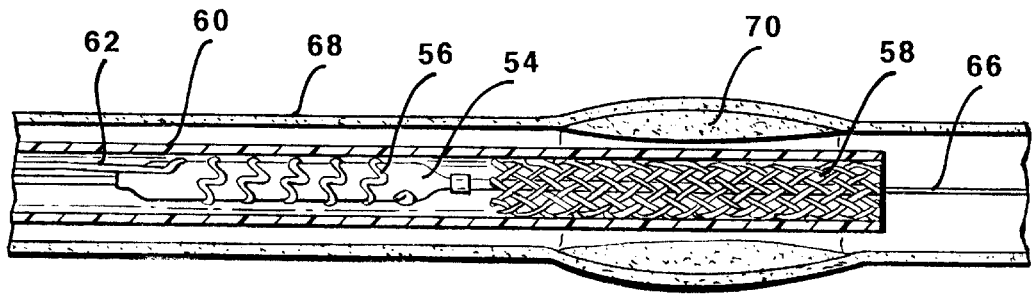
Figure 19C:
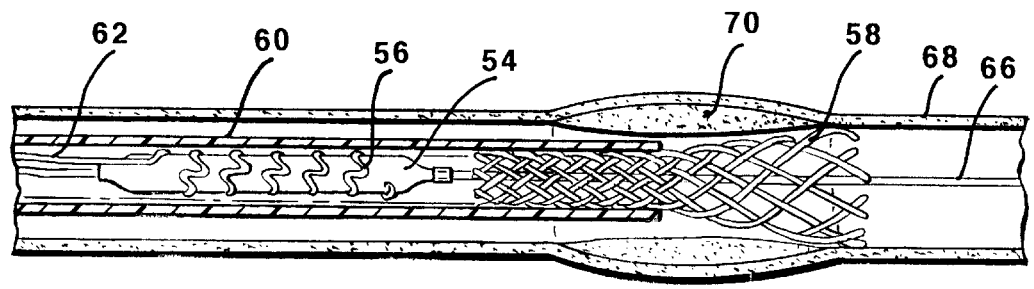
Figure 19D:
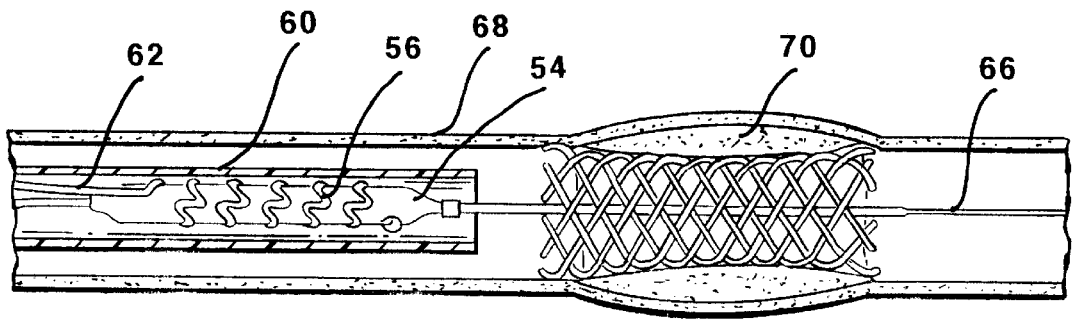
Figure 19E:
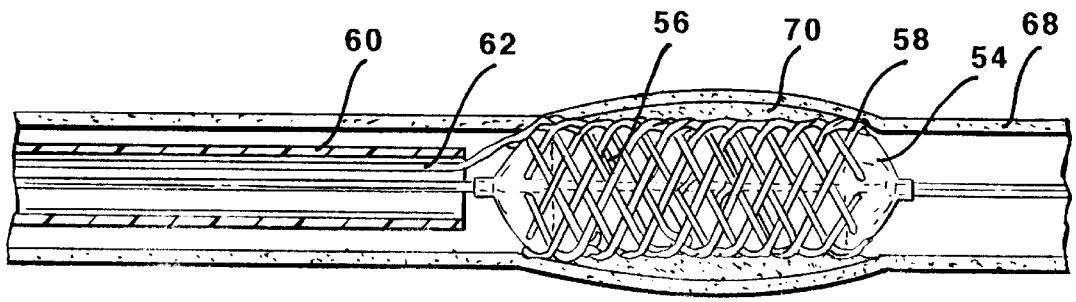
Figure 19F:
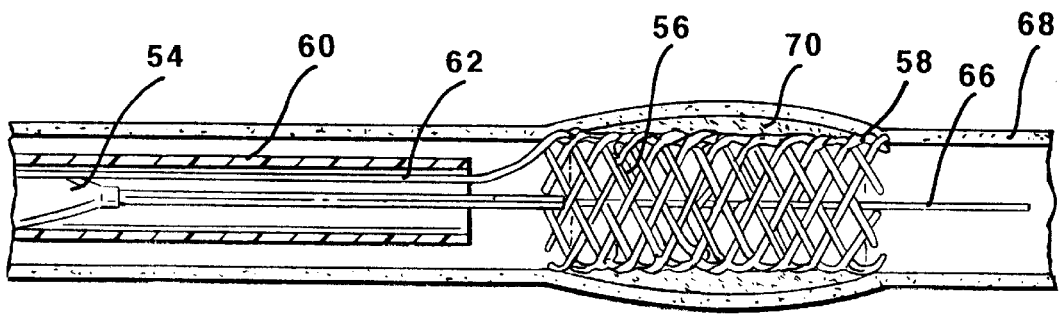
Figure 19G:
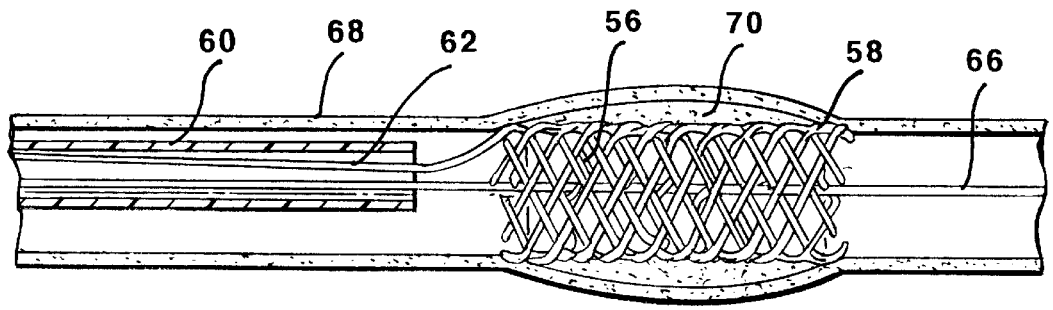
Figure 19H:
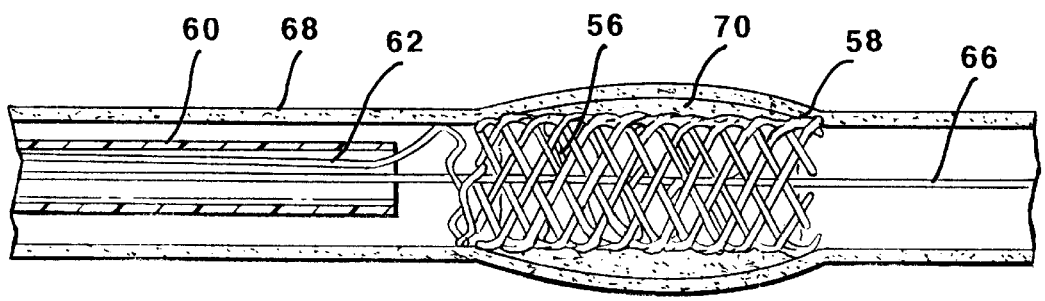
Figure 19I:
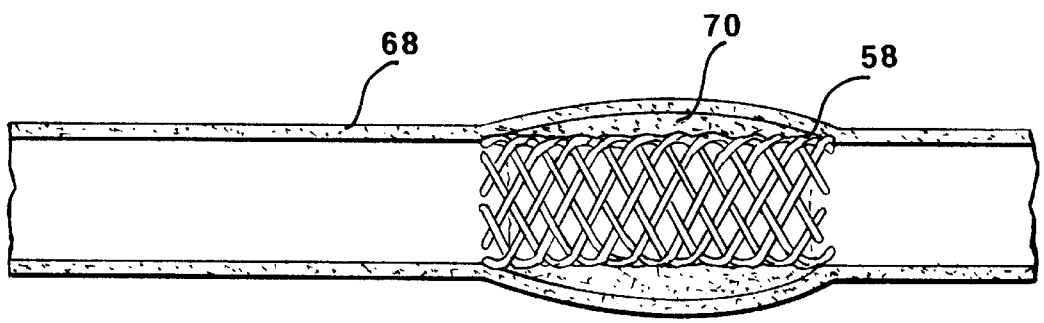

There are many options for fabricating the drug eluting stents. One option is to have all sixteen (16) filaments be drug eluting. Or, you could have any number of filaments up to sixteen (16) degrade and elute drugs. Another option is to have a multi-filar stent. Instead of a single filament braided into the stent, it is possible to have two (2), three (3), or even four (4) strands 16 braided to form a filament 12 as shown in FIG. 16. This would create a stent with much greater expansile force, but also have much more material in the surface area. This is a common trade-off in stent design. Similar to the single-filar design, the multi-filar form shown in FIG. 16 could have varying numbers of strands 16 that are drug eluting. FIGS. 16 and 17 show that the multi-filar design may be braided or unbraided. One (1), two (2), three (3), or four (4) of the filaments could be impregnated with a drug and biodegradably elute. Alternatively, the polymer may be biostable which allows for diffusion of the drug without degradation.

Figure 12:
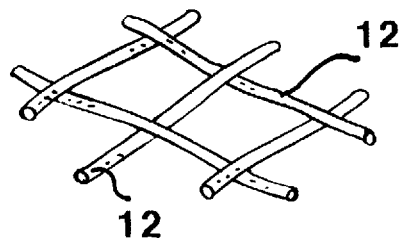
FIG. 12 is a greatly enlarged fragment of a loose weave of prosthesis filaments.
Figure 13:
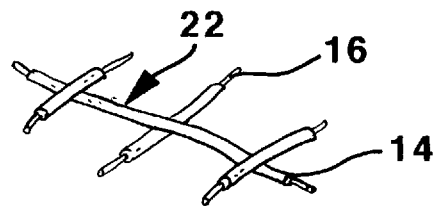
FIG. 13 is a greatly enlarged fragment of a coated metal filament in a loose weave.
Figure 14:
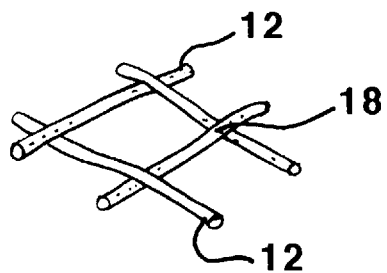
FIG. 14 is a greatly enlarged fragment of a melted junction weave of prosthesis filaments in a loose weave.
Figure 15:
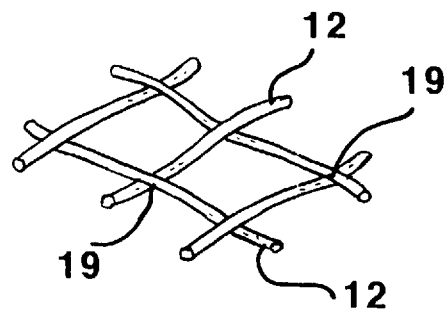
FIG. 15 is a greatly enlarged fragment of a kinked junction wave of prosthesis filaments.

The stent 10 of FIG. 1 consists of a wound braided mesh which is self-expanding to a predetermined diameter and whose profile diameter can be greatly reduced for catheter introduction. The radial expansile force increases with diameter to the point of the self-expanded diameter limit, at which point the angle between the filaments and the longitudinal axis is a maximum. FIGS. 12 and 15 show alternative construction techniques to alter the radial expansive force. FIG. 12 shows the filaments 12 being woven without any connection. FIG. 13 is similar except the filament 22 is formed with a metal core 16 and a coating 14. In FIG. 14 the individual filaments 12 are shown with a bonded juncture 18. The bonding at the juncture 18 prevents the individual filaments 12 from sliding relative to each other, which improves the radial strength. The mechanically kinked junction 19 shown in FIG. 15 also limits the sliding of the filaments to change the radial strength. A heated platen press may be pressed against the wound stent while still on the forming mandrel to form the kinks. Higher temperatures may be used to form the melted junctures 18.

The devices may be made more visible under fluoroscopy and x-ray by incorporating radiopaque materials into marker band 24 to the individual filaments 12 at the ends of the stent 10 as shown in FIG. 1. Such marker bands could help to locate the stent and assure proper placement and patency.

Bioabsorbable Prosthesis (Stent) Materials

Controlled release, via a bioabsorbable polymer, offers to maintain the drug level within the desired therapeutic range for the duration of the treatment. In the case of stents, the prosthesis materials will maintain vessel support for at least two weeks or until incorporated into the vessel wall even with bioabsorbable, biodegradable polymer constructions.

Several polymeric compounds that are known to be bioabsorbable and hypothetically have the ability to be drug impregnated may be useful in prosthesis formation herein. These compounds include: poly-1-lactic acid/polyglycolic acid, polyanhydride, and polyphosphate ester. A brief description of each is given below.

Poly-1-lactic acid/polyglycolic acid has been used for many years in the area of bioabsorbable sutures. It is currently available in many forms, i.e., crystals, fibers, blocks, plates, etc. These compounds degrade into non-toxic lactic and glycolic acids. There are, however, several problems with this compound. The degradation artifacts (lactic acid and glycolic acid) are slightly acidic. The acidity causes minor inflammation in the tissues as the polymer degrades. This same inflammation could be very detrimental in coronary and peripheral arteries, i.e., vessel occlusion. Another problem associated with this polymer is the ability to control and predict the degradation behavior. It is not possible for the biochemist to safely predict degradation time. This could be very detrimental for a drug delivery device.

Another compound which could be used are the polyanhydrides. They are currently being used with several chemotherapy drugs for the treatment of cancerous tumors. These drugs are compounded into the polymer which is molded into a cube-like structure and surgically implanted at the tumor site.

Polyanhydrides have weaknesses in their mechanical properties, due to low molecular weights. This drawback makes them difficult to process into a filament form. Also, polyanhydrides have poor solubility, making characterization and fabrication difficult.

The compound which is preferred is a polyphosphate ester. Polyphosphate ester is a compound such as that disclosed in U.S. Pat. Nos. 5,176,907; 5,194,581; and 5,656,765 issued to Leong which are incorporated herein by reference. Similar to the polyanhydrides, polyphoshate ester is being researched for the sole purpose of drug delivery. Unlike the polyanhydrides, the polyphosphate esters have high molecular weights (600,000 average), yielding attractive mechanical properties. This high molecular weight leads to transparency, and film and fiber properties. It has also been observed that the phosphorous-carbon-oxygen plasticizing effect, which lowers the glass transition temperature, makes the polymer desirable for fabrication.

The basic structure of polyphosphate ester monomer is shown below.

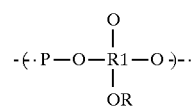

where P corresponds to Phosphorous,

O corresponds to Oxygen, and R and R1 are functional groups. Reaction with water leads to the breakdown of this compound into monomeric phosphates (phosphoric acid) and diols (see below).

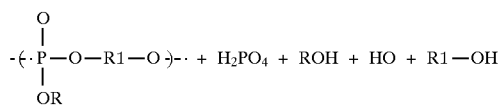

It is the hydrolytic instability of the phosphorous ester bond which makes this polymer attractive for controlled drug release applications. A wide range of controllable degradation rates can be obtained by adjusting the hydrophobicities of the backbones of the polymers and yet assure biodegradability.

The functional side groups allow for the chemical linkage of drug molecules to the polymer. This is shown below.

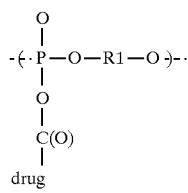

The drug may also be incorporated into the backbone of the polymer.

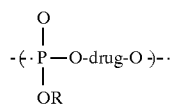

In summary, the highly hydrolytically reactive phosphorous ester bond, the favorable physical properties, and the versatile chemical structure make the polyphosphate esters a superior drug delivery system for a prosthesis.

Figure 3A:
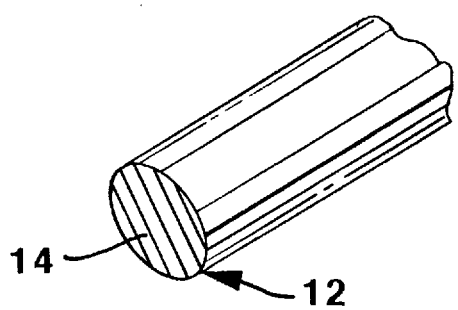
FIG. 3A is a greatly enlarged fragment of the embodiment of FIG. 1.
Figure 3B:
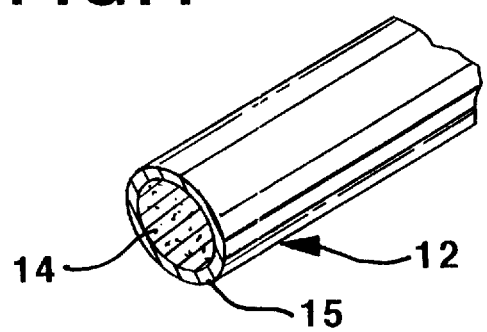
FIG. 3B is a greatly enlarged fragment of the embodiment of FIG. 1 in which two layers of polymers are present, each having a different drug.

FIGS. 3A and 3B show that the filaments 12 may be made from one or several layers of polymer. In FIG. 3A only a single polymer is present to carry the drugs. In FIG. 3B a second layer of polymer 15 is shown. That layer 15 may be a simple barrier which limits diffusion of drugs in the polymer 14. In that event, the smaller molecules could elute out immediately, while larger compounds would not elute until later when the layer 15 has biodegraded. Alternatively, layer 15 may include a different drug incorporated therein from that found in layer 14. The barrier coating 15 could be as simple as a silicone or polyurethane.

Operation

The prosthesis is inserted into the lumen wherever needed as per the usual procedure for stents. The device is fixed into place either by radial expansion in devices such as shown in FIG. 1 or are deformed by a balloon catheter in the case of devices in accordance with FIG. 2.

FIGS. 8 through 11 show the placement and effects of the drug-eluting prosthesis of the invention. The prosthesis tacks up any intimal flaps and tears caused by any prior ballooning. The initial deposition of platelets and subsequent thrombus formation 38 is controlled and minimized by the stent design and the elution which limits platelet aggregation and other immediate repair responses described previously. Localized thrombus formations in the areas of cracked and roughened plaques and newly exposed underlying collagen and fibro-muscular tissues is also decreased. This results in limited but quick neointima formation 40 and intimal proliferation over individual stent filaments progressing to mature endothelial lining. Long term significant restenosis is therefore limited. Elution of the anti-replicates along or in conjunction with the initial elution of anti-coagulants can also limit the extent of the restenosis which occurs in the natural healing process.

In yet another embodiment of the invention, a purely polymeric prosthesis such as that having the configuration shown in FIG. 1 can be combined with an expandable metal stent to provide additional support for the prosthesis. This can be important since preferred bioabsorbable polymeric materials for the prosthesis may have insufficient resilience to expand an occluded body lumen or to maintain its expansion. By including a metal stent within the lumen of the polymeric prosthesis, the polymeric prosthesis is effectively held against the wall of the body lumen by the strength of the metal stent. In a most preferred aspect of this embodiment, the metal stent is only temporarily implanted so that only the bioabsorbable prosthesis remains implanted in the body lumen on a long term basis. This can be accomplished by including a polymeric stent body and a metal stent body on the distal end of a catheter designed to expand and release the stents. Both of the stent bodies have a number of support elements which make up an open-ended, radially expandable self-supporting tubular structure. In the polymeric stent structure, a bioabsorbable polymeric element (such as a filment made from a bioabsorbable polymer) having drugs incorporated therein can be attached to the support elements of the body so that at least a portion of the bioabsorbable element is exposed at the exterior surface of the polymeric stent body. The stents are arranged on the distal end of the catheter such that the catheter can provide remote, transluminal deployment of the stents, with the metal stent inside the polymeric stent, from an entry point into a selected portion of the body lumen to be treated and also remote actuation of an expansion mechanism from the proximal end of the catheter. The expansion mechanism (e.g. a balloon or the like if the metal stent is made of malleable metal for balloon expansion or a release mechanism if the metal stent is a self-expanding stent made from a resilient metal) is one capable of providing radial expansion of the metal stent body to bring the metal stent into supporting contact with the polymeric stent body and also to press the polymeric stent body so that it expands radially into contact with the wall of the body lumen. This will bring the bioabsorbable element into supporting contact with a body lumen at an interior portion of the body lumen to be treated and will position the bioabsorbable element to deliver drugs to the body lumen. Following the expansion of the stents into luminal contact, the balloon (if the expansion device is a balloon) can be deflated which allows luminal flow to be restored. After the stents have been in place for a predetermined period of time, the metal stent can be removed to leave only the polymeric stent (and its drug delivery component) in position in the body lumen. This can be accomplished, for example, by radially contracting the metal stent and then withdrawing it from the body lumen or by unwinding the metal stent a bit at a time as it is withdrawn from the body lumen.

Referring now to specific embodiments shown in the drawings, one possible configuration for a polymeric prosthesis supported by a metal stent is that of the prosthesis shown in FIG. 1 supported by a metal stent having a configuration such as that taught in U.S. Pat. No. 4,886,062 to Wiktor which is incorporated herein by reference. These devices may be combined by simply placing the polymeric prosthesis over the metal stent and balloon; introducing the prosthesis, stent, and balloon into the body lumen as a unit until it reaches the desired point for expansion; inflating the balloon to radially expand the prosthesis and stent into contact with the body lumen; and removing the balloon. In such an embodiment, the metal stent would be permanently implanted with the polymeric prosthesis. Another embodiment of this concept is shown in FIGS. 18 and 19a–19i in which the metal stent is only implanted for a limited period of time and then removed. Referring now to FIGS. 18 and 19a–19i, a catheter assembly 50 includes a hub assembly 52 at a proximal end, an inflatable balloon 54, a metal stent 56 and a polymeric prosthesis 58 at a distal end and a sheath 60 extending from the proximal to the distal end. The metal stent 56 is crimped onto the balloon 54 and includes an elongated lead 62 extending to the proximal end of the catheter assembly 50 where it includes an enlarged portion 64 to enable an operator to securely grip the lead 62. Distal to the balloon 54 is the polymeric prosthesis 58 which is constrained from radial self-expansion by the sheath 60. In operation, a guidewire 66 is inserted into the body lumen 68 and through the point of occlusion 70. The catheter assembly 50 is then passed into the lumen 68 on the guidewire 66 until the prosthesis 58 is positioned at the point of the occlusion 70. The sheath 60 is then drawn back, thereby allowing the prosthesis 58 to be pushed out of the sheath 60 by the leading edge of the balloon assembly where it radially self-expands into luminal contact. The balloon 54 and stent 56 are then advanced out of the sheath 60 as a unit and into the open center of the prosthesis 58. The balloon 54 is then inflated to expand the metal stent 56, the prosthesis 58 and the occlusion 70. The balloon 54 is then deflated and withdrawn from the metal stent 56 and prosthesis 58, leaving the metal stent 56 inside the prosthesis 58 in support of the prosthesis 58 and the occlusion 70. If the body lumen 68 is a blood vessel, blood flow is restored by deflating the balloon 54. If desired, the balloon 54 can then be withdrawn entirely from the sheath 60 and also, if desired, the sheath 60 and guidewire 66 can be withdrawn. However, it is preferred to leave the balloon 54, sheath 60 and guidewire 66 in place in order to provide support for the lead 62 and to avoid entangling the lead 62 with the catheter lumen or guidewire 66 as they are withdrawn. If the balloon 54 or guidewire 66 are to be withdrawn, it may be preferable to modify the sheath 60 by providing a separate lumen in the sheath 60 or another location in the catheter assembly 50 for the lead 62. After a desired period of time which allows the prosthesis to achieve a stable support for the lumen, the lead 62 is pulled at the proximal end of the catheter assembly 50, thereby causing the metal stent 56 to unwind and be taken up into the sheath 60. The metal stent chosen for use in this method should include no edges or ends which can snag the prosthesis 58 and pull it from its intended position in the body lumen 68. The sheath is then withdrawn, leaving the prosthesis 58 in place in the lumen 68.

This completes the description of the preferred and alternate embodiments of the invention. Those skilled in the art may recognize other equivalents to the specific embodiments described herein which equivalents are intended to be encompassed by the claims attached hereto.

We claim:

1. A device for local intralumenal administration of drugs comprising:
   (a) a catheter having proximal and distal ends;
   (b) a first body in the form of an open-ended, radially expandable, self-supporting tubular structure, said first tubular body mounted on the catheter at the distal end thereof;
   (c) a second body having a polymer with a drug compounded therein, the second body in the form of an open-ended, radially expandable tubular structure having an interior surface and an exterior surface, at least a portion of the polymer exposed at the exterior surface thereof, said second tubular body mounted on the catheter at the distal end thereof;
   (d) means at the proximal end of the catheter for radially expanding the first and second tubular bodies to bring the self-supporting structure of the first tubular body into coaxial supporting contact with the interior surface of the second tubular body such that the polymer exposed at the exterior surface of the second tubular body contacts an interior portion of the body lumen to be treated.

2. The device of claim 1 wherein the first tubular body is helically wound.

3. The device of claim 1 wherein the polymer is a bioabsorbable polymer.

4. The device of claim 1 wherein the first tubular body is made from a deformable metal.

5. The device of claim 1 wherein the first tubular body is made from a resilient metal.

6. The device of claim 1 wherein the first tubular body includes an elongated lead that permits the tubular body to be removed following implantation.

7. The device of claim 3 wherein the bioabsorbable polymer is selected from the group consisting of polylactic acid, polyglycolic acid, polyanhydride, and polyphosphate ester.

8. The device of claim 1 wherein the polymer is a biostable polymer.

9. The device of claim 8 wherein the biostable polymer is selected from the group consisting of silicone and polyurethane.

10. The device of claim 1 wherein the drug is an anti-platelet drug.

11. The device of claim 1 wherein the drug is an anticoagulant drug.

12. The device of claim 11 wherein the anticoagulant drug is selected from the group consisting of heparin, coumadin, protamine and hirudin.

13. The device of claim 1 wherein the drug is an anti-replicate drug.

14. The device of claim 13 wherein the anti-replicate drug is selected from the group consisting of methotrexate, colchicine, azathioprine, vincristine, vinblastine, fluorouracil, adriamycin, and mutamycin.

15. The device of claim 1 wherein the drug is an anti-inflammatory drug.

16. The device of claim 15 wherein the anti-inflammatory drug is a glucocorticoid.

17. The device of claim 1 wherein the polymer is adapted to release the incorporated drug in the body lumen over a period of 4 to 6 months.

18. The device of claim 1 wherein the polymer is adapted to release the incorporated drug by elution of the drug.

19. The device of claim 1 wherein the polymer is adapted to degrade in the body lumen to release the incorporated drug.

20. The device of claim 1 wherein the first body is attached to the second body.

21. The device of claim 20 wherein the first body is interwoven with the second body.

22. The device of claim 1 wherein the second body comprises a plurality of polymeric filaments which are woven together.

23. The device of claim 22 wherein the polymeric filaments are bonded together at a juncture.

24. The device of claim 23 wherein the bonding is accomplished by heating the polymeric filaments.

25. A device for local intralumenal administration of drugs comprising:
   (a) a catheter having proximal and distal ends;
   (b) a first body in the form of an open-ended, radially expandable, self-supporting tubular structure, said first tubular body mounted on the catheter at the distal end thereof;
   (c) a second body having a polymer with a drug compounded therein and a barrier coating of polymeric material on the polymer such that the barrier coating can limit the rate of drug elution, the second body in the form of an open-ended, radially expandable tubular structure having an interior surface and an exterior surface, at least a portion of the polymer and barrier material exposed at the exterior surface thereof, said second tubular body mounted on the catheter at the distal end thereof;

(d) means at the proximal end of the catheter for radially expanding the first and second tubular bodies to bring self-supporting structure of the first tubular body into coaxial supporting contact with the interior surface of the second tubular body such that the polymer and barrier material exposed at the exterior surface of the second tubular body contacts an interior portion of the body lumen to be treated.

26. The device of claim 25 wherein the polymer is a biostable polymer.

27. The device of claim 26 wherein the biostable polymer is selected from the group consisting of silicone and polyurethane.

28. The device of claim 25 wherein the drug is an antiplatelet drug.

29. The device of claim 25 wherein the drug is an anticoagulant drug.

30. The device of claim 26 wherein the anticoagulant drug is selected from the group consisting of heparin, coumadin, protamine and hirudin.

31. The device of claim 25 wherein the drug is an anti-replicate drug.

32. The device of claim 31 wherein the anti-replicate drug is selected from the group consisting of methotrexate, colchicine, azathioprine, vincristine, vinblastine, fluorouracil, adriamycin, and mutamycin.

33. The device of claim 25 wherein the incorporated drug is an anti-inflammatory drug.

34. The device of claim 33 wherein the anti-inflammatory drug is a glucocorticoid.

35. The device of claim 25 wherein the polymer and barrier coating is adapted to release the incorporated drug in the body lumen over a period of 4 to 6 months.

36. The device of claim 25 wherein the polymer is adapted to release the drug by elution of the drug.

37. The device of claim 25 wherein the polymer is adapted to degrade in the body lumen to release the drug.

38. The device of claim 25 wherein the first body is attached to the second body.

39. The device of claim 38 wherein the first body is interwoven with the second body.

40. The device of claim 25 wherein thee second body comprises a plurality of polymeric filaments which are woven together.

41. The device of claim 40 wherein the polymeric filaments are bonded together at a juncture.

42. The device of claim 41 wherein the bonding is accomplished by heating the polymeric filaments.

43. The device of claim 25 wherein the barrier layer includes a polymer selected from the group consisting of silicone and polyurethane.

44. A device for local intralumenal administration of drugs comprising:

(a) a catheter having proximal and distal ends;

(b) a first body in the form of an open-ended, radially expandable, self-supporting tubular structure, said first tubular body mounted on the catheter at the distal end thereof;

(c) a second body having a polymer with a drug compounded therein, the second body in the form of a helically wound, open-ended, radially expandable tubular structure having an interior surface and an exterior surface and a first end and a second end, the second tubular body being variable in radial diameter under axial movement of the first and second ends relative to each other and having at least a portion of the polymer exposed at the exterior surface, said second tubular body mounted on the catheter at the distal end thereof;

(d) means at the proximal end of the catheter for radially expanding the first and second tubular bodies to bring the self-supporting tubular structure of the first tubular body into coaxial supporting contact with the interior surface of the second tubular body such that the polymer exposed at the exterior surface of the second tubular body contacts an interior portion of the body lumen to be treated.

45. The device of claim 44 wherein the first tubular body is helically wound.

46. The device of claim 44 wherein the helically wound structure is made from a bioabsorbable polymer.

47. The device of claim 44 wherein the polymer is a bioabsorbable polymer.

48. The device of claim 44 wherein the first tubular body is made from a deformable metal.

49. The device of claim 44 wherein the first tubular body is made from a resilient metal.

50. The device of claim 44 wherein the first tubular body includes an elongated lead that permits the first tubular body to be removed following implantation.

51. The device of claim 44 wherein the polymer is a biostable polymer.

52. The device of claim 51 wherein the biostable polymer is selected from the group consisting of silicone and polyurethane.

53. The device of claim 44 wherein the drug is an antiplatelet drug.

54. The device of claim 44 wherein the drug is an anticoagulant drug.

55. The device of claim 54 wherein the anticoagulant drug is selected from the group consisting of heparin, coumadin, protamine and hirudin.

56. The device of claim 44 wherein the drug is an anti-replicate drug.

57. The device of claim 56 wherein the anti-replicate drug is selected from the group consisting of methotrexate, colchicine, azathioprine, vincristine, vinblastine, fluorouracil, adriamycin, and mutamycin.

58. The device of claim 44 wherein the incorporated drug is an anti-inflammatory drug.

59. The device of claim 58 wherein the anti-inflammatory drug is a glucocorticoid.

60. The device of claim 44 wherein the polymer is adapted to release the incorporated drug in the body lumen over a period of 4 to 6 months.

61. The device of claim 44 wherein the polymer is adapted to release the drug by elution of the drug.

62. The device of claim 44 wherein the polymer is adapted to degrade in the body lumen to release the drug.

63. The device of claim 44 wherein the first body is attached to the second body.

64. The device of claim 63 wherein the first body is interwoven with the second body.

65. The device of claim 44 wherein the second body comprises a plurality of polymeric filaments which are woven together.

66. The device of claim 65 wherein the polymeric filaments are bonded together at a juncture.

67. The device of claim 66 wherein the bonding is accomplished by heating the polymeric filaments.

68. The device of claim 1 wherein the means for radially expanding the first and second tubular bodies comprises a balloon.

69. The device of claim 1 wherein the first body is a self-expanding metal stent, and wherein the means for radially expanding the first and second tubular bodies comprises a release mechanism.

70. The device of claim 25 wherein the means for radially expanding the first and second tubular bodies comprises a balloon.

71. The device of claim 25 wherein the first body is a self-expanding metal stent, and wherein the means for radially expanding the first and second tubular bodies comprises a release mechanism.

72. The device of claim 44 wherein the means for radially expanding the first and second tubular bodies comprises a balloon.

73. The device of claim 44 wherein the first tubular body is a self-expanding metal stent, and wherein the means for radially expanding the first and second tubular bodies comprises a release mechanism.

* * * * *